United States Patent [19]
Graff et al.

[11] Patent Number: 6,001,128
[45] Date of Patent: Dec. 14, 1999

[54] MATERIALS FOR USE IN GLAUCOMA FILTRATION DEVICES

[75] Inventors: Gustav Graff, Cleburne; Mutlu Karakelle; John W. Sheets, Jr., both of Fort Worth; John M. Yanni, Burleson, all of Tex.

[73] Assignee: Alcon Laboratories, Inc., Fort Worth, Tex.

[21] Appl. No.: 09/086,883

[22] Filed: May 29, 1998

Related U.S. Application Data

[60] Provisional application No. 60/047,882, May 29, 1997.

[51] Int. Cl.$^6$ ....................................................... A61F 2/16
[52] U.S. Cl. ................................. 623/6; 623/4; 623/901; 210/348; 210/500.35; 606/161
[58] Field of Search .................. 210/500.27, 500.35, 210/348; 604/8, 9, 294; 526/259; 623/4, 6, 901; 606/161

[56] References Cited

U.S. PATENT DOCUMENTS

| | | | |
|---|---|---|---|
| 4,936,850 | 6/1990 | Barrett | 623/6 |
| 5,066,401 | 11/1991 | Müller et al. | 210/500.35 |
| 5,171,267 | 12/1992 | Ratner et al. | 623/6 |
| 5,236,588 | 8/1993 | Zhang et al. | 210/500.35 |
| 5,282,855 | 2/1994 | Bragg | 623/6 |
| 5,290,892 | 3/1994 | Namdaran et al. | 526/259 |
| 5,476,445 | 12/1995 | Baerveldt et al. | 604/8 |
| 5,529,690 | 6/1996 | Pashley et al. | 210/490 |
| 5,652,014 | 7/1997 | Galin et al. | 623/6 |

FOREIGN PATENT DOCUMENTS

| | | |
|---|---|---|
| 0 485 197 A1 | 5/1992 | European Pat. Off. . |
| WO 95/35078 | 12/1995 | WIPO . |

OTHER PUBLICATIONS

Hoskins, et al., "Filtering Seton Implant for Glaucoma: Initial Animal Trial," *Ophthalmol*, vol. 102, pp. 894–904 (1995).

Prata, Jr., et al., "In Vitro and In Vivo Flow Characteristics of Glaucoma Drainage Implants," *Ophthalmic Surgery*, vol. 23, pp. 702–707 (1992).

*Primary Examiner*—Ana Fortuna
*Attorney, Agent, or Firm*—Patrick M. Ryan

[57] ABSTRACT

Improved glaucoma filtration device materials comprise at least one monomer having the formula:

$$CH_2{=}\overset{X}{\underset{|}{C}}{-}COO{-}(CH_2)_{\overline{m}}{-}Y{-}R$$

wherein:
  X is H or $CH_3$;
  m is 0–10;
  Y is nothing, O, or S;
  R is nothing, H, or an aliphatic, aromatic or aliphatic/aromatic combination of up to twelve carbon atoms, which can be unsubstituted or substituted with Cl, F, Br, or an alkoxy of up to four carbon atoms; and
a cross-linking monomer having two or more ethylenically unsaturated groups.

7 Claims, No Drawings

MATERIALS FOR USE IN GLAUCOMA FILTRATION DEVICES

This application claims priority from co-pending provisional application, U.S. patent application Ser. No. 60/047,882, filed May 29, 1997.

FIELD OF THE INVENTION

The present invention relates to the field of ophthalmology. More specifically, the invention relates to polymeric materials for use in the manufacture of glaucoma filtration devices.

BACKGROUND OF THE INVENTION

The underlying causes of glaucoma are not fully understood. However, it is known that elevated intraocular pressure is one of the symptoms associated with the development of glaucoma. Elevations of intraocular pressure can ultimately lead to impairment or loss of normal visual function due to damage to the optic nerve. It is also known that the elevated intraocular pressure is caused by an excess of fluid (i.e., aqueous humor) within the eye. The excess intraocular fluid is believed to result from blockage or impairment of the normal drainage of fluid from the eye via the trabecular meshwork.

The current drug therapies for treating glaucoma attempt to control intraocular pressure by means of increasing the drainage or "outflow" of aqueous humor from the eye or decreasing the production or "inflow" of aqueous humor by the ciliary processes of the eye. In some cases, patients become refractory to drug therapy. In other cases, the use of drug therapy alone is not sufficient to adequately control intraocular pressure, particularly if there is a severe blockage of the normal passages for the outflow of aqueous humor. Thus, some patients require surgical intervention to correct the impaired outflow of aqueous humor and thereby normalize or at least control their intraocular pressure. The outflow of aqueous humor can be improved by means of intraocular surgical procedures known to those skilled in the art as trabeculectomy procedures. These procedures are collectively referred to herein as "glaucoma filtration surgery."

The procedures utilized in glaucoma filtration surgery generally involve the creation of a fistula to promote the drainage of aqueous humor into a surgically prepared filtration bleb. Alternatively, filtration devices have been used to shunt aqueous humor via a cannula from the anterior chamber into a dispersing device implanted beneath a surgically created bleb. A number of designs for filtration implants are known. See, for example, Prata et al., Ophthalmol. 102:894–904 (1995) which reviews a variety of available filtration implants made from polypropylene, polymethylmethacrylate or silicone materials. See also, Hoskins et al., Ophthalmic Surgery 23:702–707 (1992).

Wound fibroplasia is a common cause of failure for glaucoma filtration devices. The fibroplasia results in encapsulation of the device, limiting aqueous humor outflow. There is a need for an improved glaucoma filtration device material which exhibits flexibility, is resistant to bioerosion and tissue adhesion, and does not elicit a significant immune response.

SUMMARY OF THE INVENTION

This invention is directed to glaucoma filtration device materials comprising one or more monomers having the following structure:

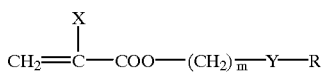

wherein:
X is H or $CH_3$;
m is 0–10;
Y is nothing, O, or S;
R is nothing, H, or an aliphatic, aromatic or aliphatic/aromatic combination of up to twelve carbon atoms, which can be unsubstituted or substituted with Cl, F, Br, or an alkoxy of up to four carbon atoms; and
a cross-linking monomer having two or more ethylenically unsaturated groups.

DETAILED DESCRIPTION OF THE INVENTION

The glaucoma filtration device material of the present invention comprises one or more monomers of Formula I:

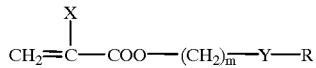

(I)

wherein:
X is H or $CH_3$;
m is 0–10;
Y is nothing, O, or S;
R is nothing, H, or an aliphatic, aromatic or aliphatic/aromatic combination of up to twelve carbon atoms, which can be unsubstituted or substituted with Cl, F, Br, or an alkoxy of up to four carbon atoms; and
a cross-linking monomer having two or more ethylenically unsaturated groups.

Suitable monomers of the above formula include, but are not limited to: 2-ethylphenoxy methacrylate; 2-ethylthiophenyl methacrylate; 2-ethylaminophenyl methacrylate; phenyl methacrylate; benzyl methacrylate; 2-phenylethyl methacrylate; 3-phenylpropyl methacrylate; 4-phenylbutyl methacrylate; 4-methylphenyl methacrylate; 4-methylbenzyl methacrylate; 2-2-methylphenylethyl methacrylate; 2-3-methylphenylethyl methacrylate; 2-4-methylphenylethyl methacrylate; 2-(4-propylphenyl)ethyl methacrylate; 2-(4-(1-methylethyl)phenyl)ethyl methacrylate; 2-(4-methoxyphenyl)ethyl methacrylate; 2-(4-cyclohexylphenyl)ethyl methacrylate; 2-(2-chlorophenyl)ethyl methacrylate; 2-(3-chlorophenyl)ethyl methacrylate; 2-(4chlorophenyl)ethyl methacrylate; 2-(4-bromophenyl)ethyl methacrylate, 2-(3-phenylphenyl)ethyl methacrylate; 2-(4-phenylphenyl)ethyl methacrylate); 2-(4-benzylphenyl)ethyl methacrylate; n-butyl methacrylate; n-hexyl methacrylate; 2-ethylhexyl methacrylate; 2-ethoxyethyl methacrylate; 2,3-dibromopropyl methylacrylate; cyclohexyl methacrylate; hydroxyethyl methacrylate; methyl methacrylate; ethyl methacrylate; trifluoromethyl methacrylate; hydroxypropyl methacrylate; 1H,1H,5H-octafluoropentyl methacrylate; 1H,1H-perfluoro-n-octyl methacrylate; 2,2,2-trifluoroethyl methacrylate; 1H,1H-heptafluoro-butyl methacrylate; 1H,1H,11H-eicosafluorodecyl methacrylate; 1H,1H,7H-dodecafluoroheptyl methacrylate; and the like, including their corresponding acrylates.

The copolymerizable cross-linking agent used in the polymers of this invention may be any ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; allyl methacrylate; 1,6-hexanediol dimethacrylate; 1,4-butanediol dimethacrylate; and the like, including their corresponding acrylates. A preferred cross-linking agent is 1,4-butanediol diacrylate (BDDA).

The glaucoma filtration device materials of the present invention may comprise homopolymers of monomers of Formula (I) or copolymers of two or more different monomers of Formula (I). It will be understood by those skilled in the art, that among polymers of acrylic esters, those made from acrylate monomers tend to have lower glass transition temperatures and to be more flexible than polymers of methacrylate. Accordingly, if a relatively flexible material is desired, the glaucoma drainage device materials of this invention will generally comprise copolymers containing a greater mole percent of acrylate monomers of Formula I, than of methacrylate monomers of Formula I. If flexible materials are desired, it is preferred that the acrylate monomers constitute from about 60 mole percent to about 95 mole percent of the material, while the methacrylate monomers constitute from about 5 mole percent to about 40 mole percent. Most preferred is a copolymer comprising about 60–70 mole percent 2-phenylethyl acrylate (PEA) wherein, in Formula (I), X is H, m is 2, Y is nothing and R is benzene; and about 30–40 mole percent 2-phenylethyl methacrylate (PEMA), wherein, in Formula (I), X is $CH_3$, m is 2, Y is nothing and R is benzene.

The proportion of the monomers is preferably chosen to produce a polymer material having a glass transition temperature not greater than about 37° C., which is normal human body temperature. Polymers having glass transition temperatures higher than 37° C. would only be flexible at temperatures above 37° C. It is preferred to use polymers having a glass transition temperature somewhat below normal body temperature and no greater than normal room temperature, e.g., about 20° C.–25° C., in order that the glaucoma filtration devices can be conveniently manipulated at room temperature.

The glaucoma filtration device materials must exhibit sufficient strength to allow them to be manipulated by the surgeon without fracturing or otherwise suffering significant damage. Polymeric materials exhibiting an elongation of at least 150% are preferred. Most preferably, the polymeric materials exhibit an elongation of at least 200%. Glaucoma filtration devices made from polymeric materials which break at less than 150% elongation may not endure the distortion which necessarily occurs when they are surgically implanted.

The polymeric materials of this invention are prepared by generally conventional polymerization methods. A mixture of the liquid monomers in the desired proportions together with a conventional thermal free-radical initiator is prepared. The mixture can then be introduced into a mold of suitable shape to form the desired glaucoma filtration device. Polymerization may be carried out by gentle heating to activate the initiator, for example. Typical thermal free radical initiators include peroxides, such as benzophenone peroxide, peroxycarbonates, such as bis-(4-t-butylcyclohexyl) peroxydicarbonate, azonitriles, such as azobisisobutyronitrile, and the like. A preferred initiator is bis-(4-t-butylcyclohexyl) peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization. Photosensitizers can be introduced as well to permit the use of longer wavelengths; however, in preparing a polymer which is intended for long residence within the eye, it is generally preferable to keep the number of ingredients in the polymer to a minimum to avoid the presence of materials which might leach from the glaucoma filtration device into the interior of the eye.

Many designs of glaucoma filtration devices are known. The polymeric materials of the present invention can be used in the manufacture of glaucoma filtration of virtually any design, including, for example, those designs known as the Molteno, Ahmed, Baerveldt, Krupin disk and OptiMed glaucoma implants. See, Prata et al., Ophthalmol. 102:894–904 (1995), the entire contents of which are hereby incorporated by reference. See also, U.S. Pat. No. 5,476,445, which discloses the Baerveldt implant in detail, but with silicone elastomeric materials rather than the acrylic materials of the present invention. For yet another known implant design, see International Publication No. WO 95135078 which discloses a sclerotomy implant. The entire contents of U.S. Pat. No. 5,476,445 and WO 95/35078 are also incorporated by reference.

The preferred filtration device material of the present invention comprises a copolymer of about 65 parts by weight PEA, 30 parts by weight PEMA and 3.2 parts by weight BDDA.

The filtration device materials of the present invention can be molded in, for example, polypropylene molds. After curing the polymeric material, the mold containing the cured material can then be shaped or cut to the desired shape. This shaped mold may then be easily mounted to carry out any contouring operations prior to removing the mold. Shaping operations may be easier to perform if the molded material is first cooled to less than 10° C. and preferably less than 0° C.

The invention will be further illustrated by the following examples which are intended to be illustrative, but not limiting.

EXAMPLE 1

These examples illustrate the preparation of materials suitable for use in the manufacture of glaucoma filtration devices.

A mixture of 90 mole percent 2-phenylethyl acrylate (PEA), 5 mole percent 2-phenylethyl methacrylate (PEMA), 5 mole percent 1–6 hexanediol dimethacrylate (HDDMA), and 0.1 percent by weight of bis-(4-t-butylcyclohexyl) peroxydicarbonate was degassed and transferred into a film mold made of two glass plates with one layer of a polyethylene terephthalate film on each facing side, with the plates being separated by a silicone gasket of 0.8 mm thickness. The mold was designed so that there would be no differential pressure buildup between the inside and the outside of the mold during the polymerization. The mold was completely filled by injecting the mixture, e.g., by means of a syringe, into a filling port until the mold was filled and excess monomer mixture was discharged through a vent.

The filled mold was then heated in an inert environment, for 15 hours at 50° C. At the end of the polymerization period, the mold was opened and the cured sheet of polymer was removed. The material was found to be soft, and foldable, with a glass transition temperature of approximately 12° C.

Additional materials were made using the above procedure but varying the proportions of the ingredients. The formulations are summarized in Table 1, Examples 1–10.

TABLE 1

| | Monomer Composition* | | | | Properties | | |
|---|---|---|---|---|---|---|---|
| Ex.# | PEA | PEMA | HDDMA | BDDA | Tg (°C.) | Elongation (%) | Tan |
| 1 | 90 | 5 | 5 | | 12 | — | 0.08 |
| 2 | 89.5 | 10 | 0.5 | | 10 | 490 | 0.16 |
| 3 | 89 | 10 | 1 | | 11 | 330 | 0.32 |
| 4 | 88.5 | 10 | 1.5 | | 10 | 200 | 0.16 |
| 5 | 88 | 10 | 2 | | 10 | 220 | 0.10 |
| 6 | 79.5 | 20 | 0.5 | | 13 | 500 | 0.45 |
| 7 | 79 | 20 | 1 | | 11 | 300 | 0.23 |
| 8 | 78.5 | 20 | 1.5 | | 11 | 220 | 0.29 |
| 9 | 78 | 20 | 2 | | 15 | 230 | 0.25 |
| 10 | 70 | 30 | | 3 | 20 | 200 | 0.25 |

PEA: 2-Phenylethyl acrylate
PEMA: 2-Phenylethyl methacrylate
HDDMA: 1-6 Hexanediol dimethacrylate
BDDA: 1-4 Butanediol diacrylate
Tg - Glass Transition Temperature
Elongation - Ultimate Elongation at 20° C.
Tan - Ratio of loss modulus over storage modulus at 37° C.
*Concentrations are expressed as weight percent in Ex. # 1–9 and parts by weight in Ex. # 10.

The glass transition temperature (Tg) was measured by differential thermal analysis using conventional equipment. The ultimate elongation was measured at 20° C. by means of a Mini-Mat elongation instrument manufactured by Polymer Labs, Inc., wherein coupons cut from the 0.8 mm thick sheets where clamped in opposing jaws which were drawn apart until the samples fractured. The refractive index at 20° C. was measured with an Abbe refractometer. The ratio of loss modulus over storage modulus (Tan) at 37° C. was measured with a Dynamic Mechanical Thermal Analyzer manufactured by Polymer Labs, Inc., wherein a sample of the 0.8 mm thick sheet was vibrated and the ratio of restoring force to exciting force was determined.

EXAMPLE 2

The following copolymers can be prepared using conventional polymerization procedures. All concentrations are expressed in parts by weight.

TABLE 2

| | 1 | 2 | 3 | 4 | 5 | 6 | 7 | 8 | 9 |
|---|---|---|---|---|---|---|---|---|---|
| PEMA | 30 | 15 | 15 | 17 | 15 | 30 | 30 | 30 | 30 |
| PEA | 65 | 80 | 80 | 80 | 80 | 65 | — | — | 65 |
| PPA | — | — | — | — | — | — | 65 | — | — |
| POEA | — | — | — | — | — | — | — | 65 | — |
| BDDA | 3.2 | 3.2 | — | — | — | — | 3.2 | 3.2 | 3.2 |
| DDDA | — | — | 3.2 | — | — | — | — | — | — |
| PE400DA | — | — | — | 3.2 | — | — | — | — | — |
| PE1000DMA | — | — | — | — | 3.2 | 10 | — | — | — |
| BZP | 1 | 1 | 1 | 1 | 1 | 1 | 1 | 1 | 1 |

Material Code
PEA 2-Phenylethyl Acrylate
PEMA 2-Phenylethyl Methacrylate
PPA 3-Phenylpropyl Acrylate
POEA 2-Phenoxyethyl Acrylate (Polysciences, caustic washed)
BDDA Butanediol Diacrylate X-Linker
DDDA 1,10 Decandediol Diacrylatex-Linker
PEG400DA Polyethyleneglycol 400 Diacrylate X-Linker
PEG1000DMA Polyethyleneglycol 1000 Dimethacrylate X-Linker
BZP Benzoyl Peroxide Though other known methods of curing would also be suitable, one method of thermally curing the materials of the present invention involves placing them into an air circulating oven for 16 to 18 hours at 65° C., followed by 3 hrs at 100° C.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A method of making a glaucoma filtration device comprising fashioning the device using a polymeric material comprising a monomer of the formula:

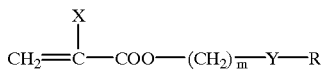

wherein:

X is H or $CH_3$;

m is 0–10;

Y is nothing, O, or S;

R is nothing, H, or an aliphatic, aromatic or aliphatic/aromatic combination of up to twelve carbon atoms, which can be unsubstituted or substituted with Cl, F, Br, or an alkoxy of up to four carbon atoms; and a cross-linking monomer having two or more ethylenically unsaturated groups.

2. The method of claim 1 wherein the monomer is selected from the group consisting of 2-ethylphenoxy methacrylate; 2-ethylthiophenyl methacrylate; 2-ethylaminophenyl methacrylate; phenyl methacrylate; benzyl methacrylate; 2-phenylethyl methacrylate; 3-phenylpropyl methacrylate; 4-phenylbutyl methacrylate; 4-methylphenyl methacrylate; 4-methylbenzyl methacrylate; 2-2-methylphenylethyl methacrylate; 2-3-methylphenylethyl methacrylate; 2-4-methylphenylethyl methacrylate; 2-(4-propylphenyl)ethyl methacrylate; 2-(4-(1-methylethyl)phenyl)ethyl methacrylate; 2-(4-methoxyphenyl)ethyl methacrylate; 2-(4-cyclohexylphenyl)ethyl methacrylate; 2-(2-chlorophenyl) ethyl methacrylate; 2-(3-chlorophenyl)ethyl methacrylate; 2-(4-chlorophenyl)ethyl methacrylate; 2-(4-bromophenyl) ethyl methacrylate, 2-(3-phenylphenyl)ethyl methacrylate; 2-(4-phenylphenyl)ethyl methacrylate); 2-(4-benzylphenyl) ethyl methacrylate; n-butyl methacrylate; n-hexyl methacrylate; 2-ethylhexyl methacrylate; 2-ethoxyethyl methacrylate; 2,3-dibromopropyl methylacrylate; cyclohexyl methacrylate; hydroxyethyl methacrylate; methyl methacrylate; ethyl methacrylate; trifluoromethyl methacrylate; hydroxypropyl methacrylate; 1H,1H,5H-octafluoropentyl methacrylate; 1H,1H-perfluoro-n-octyl methacrylate; 2,2,2-trifluoroethyl methacrylate; 1H,1H-heptafluoro-butyl methacrylate; 1H,1H,11H-eicosafluorodecyl methacrylate; 1H,1H,7H-dodecafluoroheptyl methacrylate; and their corresponding acrylates.

3. The method of claim 1 wherein the polymeric material comprises two or more monomers of the formula:

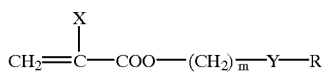

wherein:

X is H or CH$_3$;

m is 0–10;

Y is nothing, O, or S;

R is nothing, H, or an aliphatic, aromatic or aliphatic/aromatic combination of up to twelve carbon atoms, which can be unsubstituted or substituted with Cl, F, Br, or an alkoxy of up to four carbon atoms.

4. The method of claim 3 wherein the polymeric material comprises an acrylate monomer and a methacrylate monomer.

5. The method of claim 4 wherein the acrylate monomer is PEA, present at a concentration of about 65 wt. %; the methacrylate monomer is PEMA, present at a concentration of about 30 wt. %; and the cross-linking monomer is 1,4-butanediol diacrylate, present at a concentration of about 3.2 wt. %.

6. The method of claim 1 wherein the cross-linking monomer is selected from the group consisting of ethylene glycol dimethacrylate; diethylene glycol dimethacrylate; allyl methacrylate; 1,3-propanediol dimethacrylate; allyl methacrylate; 1,6-hexanediol dimethacrylate; 1,4-butanediol dimethacrylate; and their corresponding acrylates.

7. The method of claim 6 wherein the cross-linking monomer is 1,4-butanediol diacrylate.

* * * * *